US009201082B2

(12) United States Patent
Chang et al.

(10) Patent No.: US 9,201,082 B2
(45) Date of Patent: Dec. 1, 2015

(54) HAND-HELD ANALYTICAL DEVICES AND METHODS OF USE THEREOF

(71) Applicant: Roche Diagnostics Operations, Inc., Indianapolis, IN (US)

(72) Inventors: Tso-Yu Chang, New Taipei (TW); Peng-Kun Wang, Hsinchu (TW)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/268,189

(22) Filed: May 2, 2014

(65) Prior Publication Data
US 2014/0242705 A1 Aug. 28, 2014

Related U.S. Application Data

(63) Continuation of application No. PCT/EP2012/071589, filed on Oct. 31, 2012.

(30) Foreign Application Priority Data

Nov. 4, 2011 (EP) .................................... 11187840

(51) Int. Cl.
G01N 35/00 (2006.01)
G01N 33/483 (2006.01)
G01N 33/48 (2006.01)
A61B 5/145 (2006.01)
A61B 5/00 (2006.01)
G01N 33/487 (2006.01)
G01N 21/84 (2006.01)

(52) U.S. Cl.
CPC ...... *G01N 35/00009* (2013.01); *A61B 5/14532* (2013.01); *G01N 21/8483* (2013.01); *G01N 33/48764* (2013.01); *G01N 33/483* (2013.01); *Y10T 436/11* (2015.01); *Y10T 436/110833* (2015.01)

(58) Field of Classification Search
CPC ................ Y10T 436/00; Y10T 436/11; Y10T 436/110833; A61B 5/14532; A61B 5/145; A61B 145/00; G01N 21/8483; G01N 21/84; G01N 21/00; G01N 35/00009; G01N 35/00; G01N 33/48764; G01N 33/4875; G01N 33/487; G01N 33/483; G01N 33/48; G01N 33/00
USPC ............................. 436/44, 43; 422/66, 63, 50
See application file for complete search history.

(56) References Cited

U.S. PATENT DOCUMENTS 6,470,291 B1 10/2002 Goker et al.
2007/0066938 A1 3/2007 Iio et al.

FOREIGN PATENT DOCUMENTS

EP 2177155 A1 4/2010
EP 2279689 A1 2/2011

OTHER PUBLICATIONS

International Search Report for PCT/EP2012/071589, Translation of the Written Opinion, obtained on Mar. 16, 2015, pp. 1-6.*

* cited by examiner

*Primary Examiner* — Christine T Mui
(74) *Attorney, Agent, or Firm* — Roche Diabetes Care, Inc.

(57) ABSTRACT

Hand-held analytical devices are provided for blood sugar tests. The devices can incorporate a replaceable test tape cassette having a test tape with a plurality of analytical aids and have a tape drive having a DC motor and gearing that can be coupled to the test tape cassette for successive provision of the analytical aids. The devices also include a control device for rotational speed control of the DC motor. Methods also are provided for operating such hand-held analytical devices.

21 Claims, 2 Drawing Sheets

HAND-HELD ANALYTICAL DEVICES AND METHODS OF USE THEREOF

CROSS-REFERENCE TO RELATED APPLICATIONS

This patent application is a continuation of Int'l Patent Application No. PCT/EP2012/071589; filed 31 Oct. 2012, which claims priority to and the benefit of EP Patent Application No. 11187840.1; filed 4 Nov. 2011. Each patent application is incorporated herein by reference as if set forth in its entirety.

TECHNICAL FIELD

This disclosure relates generally to engineering and medicine, and more particularly, it relates to hand-held medical devices for blood sugar testing that include a DC motor and a control device for controlling rotational speed of the DC motor.

BACKGROUND

Hand-held analytical devices and test tape systems have been proposed in a series of patent applications by the Applicant and to obtain further user advantages over the strip systems available on the market. For practical purposes, besides reliable positioning of the test elements, it is also necessary to ensure that it is possible to comply with a predetermined provision time for the individual tests with the least possible outlay.

For the foregoing reasons, there is a need for hand-held analytical devices having improved control over test tape speed.

BRIEF SUMMARY

This disclosure describes hand-held analytical devices and methods of use thereof. An inventive concept described herein includes supplementing a high-speed motor with rotational speed control that is as simple as possible. Accordingly, it is proposed that the hand-held devices include a control device having a rotary pickup arranged on the DC motor to record actual rotational speed of a motor drive shaft. In this manner, it is possible to use economical, compact, low-power motors and to compensate for their design-related rotational speed variance without motor calibration having been necessary during production. At the same time, the motor rotational speed can be controlled usage-dependently in such a way that a constant test tape speed and therefore a constant test provision time are achieved. Direct recording of the rotation of the motor drive shaft allows the required accuracy of the control with a short dead time, the discovery being based on the fact that no significant interfering effects occur owing to the drive coupling of the test tape downstream of the motor.

It therefore is an object of the disclosure to improve the systems and methods proposed in the prior art, and to achieve rapid analytical aid provision with tolerable tape loading by simple means.

In one aspect, hand-held analytical devices are provided. The devices include a replaceable test tape cassette having a test tape with a plurality of analytical aids. In addition, the devices include a tape drive having a DC motor and gearing that can be coupled to the test tape cassette for successively providing the analytical aids. Furthermore, the devices include a control device for controlling rotational speed of the DC motor.

In some instances, the control device includes a rotary pickup arranged on the DC motor. To permit highly precise recording of rotation angle with the simplest possible means, it is advantageous for the rotary pickup to include an optoelectronic encoder optically sampling the rotation of a motor drive shaft while generating a rate of electrical pulses proportional to the rotational speed as an output signal. In other instances, the rotary pickup includes an interrupter, such as a vaned wheel or a perforated disk, seated in a rotationally fixed manner on the motor drive shaft and a light barrier fixed to the device and interacting with the interrupter, such as a fork light barrier.

In some instances, the control device includes a comparator for forming a control difference between actual rotational speed and a setpoint rotational speed specified as a control variable. In other instances, the control device also can include a control processor, to which a control difference can be applied on the input side, for adjusting a setpoint rotational speed in a closed control loop. In yet other instances, and for a fastest possible reduction of a control deviation, the control processor includes proportional and integral control elements formed by a software routine.

For the most precise signal evaluation possible, the control device can include a clock generator for generating time clock pulses and a counter for counting time clock pulses between two signal edges of an output signal of the rotary pickup.

For accurate control variable adjustment, the control device can include a pulse-width modulator as an actuating element for driving the DC motor with a pulse-width modulated DC voltage.

In some instances, the control device is adapted to achieve a tape speed of the test tape of about 15±2 mm/s with an adjustment time in a range from about 0.1 s to about 0.25 s.

In some instances, the control device includes a setpoint value generator for establishing a current setpoint rotational speed in accordance with a constant provision time for the respective provision of the analytical aids. In this manner, the control device also can include a setpoint value memory for storing a setpoint value table, in which a value of the setpoint rotational speed of the DC motor is respectively assigned to a test number of the continuously numbered analytical aids.

For usage information, even in the event of a test tape cassette change, the test tape cassette includes a storage means, such as an RFID chip, for usage-dependent storage of a test number of the analytical aid currently to be provided.

In some instances, the test tape drive is adapted to draw the analytical aids when required by tape transport from a stock spool shielded from the surroundings and to provide them at an application site of a device housing.

In view of the foregoing, methods are provided for using the hand-held analytical devices as described herein. The methods can include the steps of providing a hand-held device as described herein with a test tape cassette having a test tape with a plurality of analytical aids and controlling a rotational speed of a DC motor of a tape drive with a control device, where the actual rotational speed of the motor drive shaft is recorded by a rotary pickup of the control device, which pickup is arranged on the DC motor (30).

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
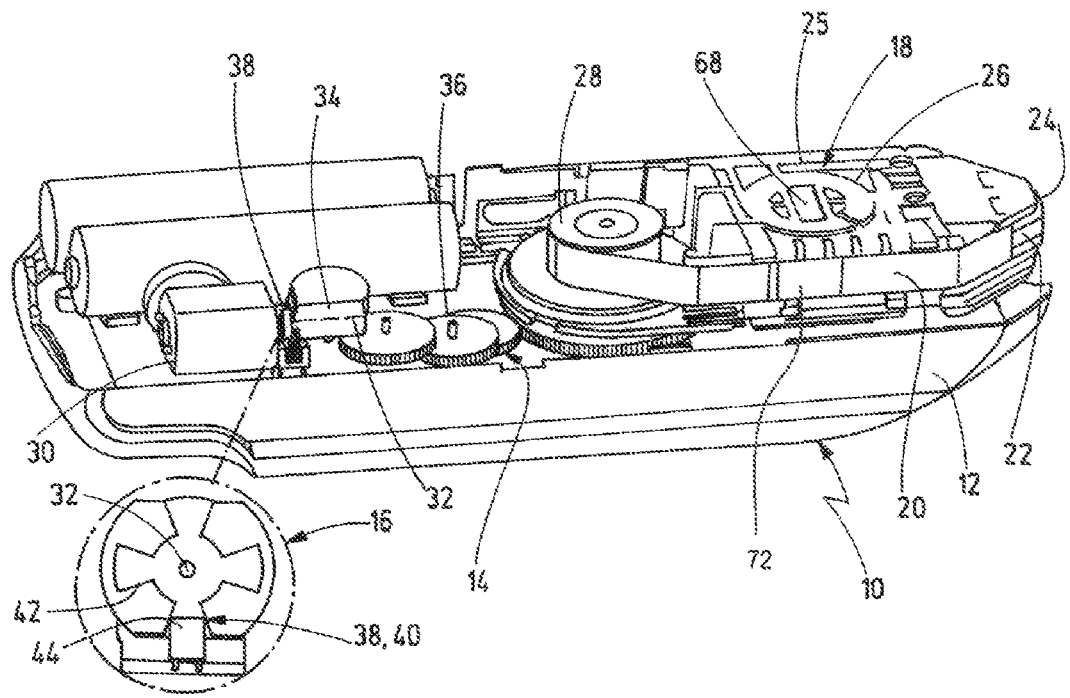
FIG. 1 shows an exemplary hand-held analytical device for use with a replaceable test tape cassette in a perspective representation with detail enlargement of an exemplary rotary pickup.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The devices and methods now will be described more fully hereinafter with reference to the accompanying drawings, in which some, but not all embodiments of the inventive concept are shown. Indeed, the devices and methods may be embodied in many different forms and should not be construed as limited to the embodiments set forth herein; rather, these embodiments are provided so that this disclosure will satisfy applicable legal requirements.

Likewise, many modifications and other embodiments of the devices and methods described herein will come to mind to one of skill in the art to which the disclosure pertains having the benefit of the teachings presented in the foregoing descriptions and the associated drawings. Therefore, it is to be understood that the devices and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the devices and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Hand-held devices are provided for use with replaceable test tape cassettes. The devices include a tape drive having a DC motor and gearing that can be coupled to the test tape cassette for successively providing analytical aids thereupon. The devices also include a control device for controlling rotational speed of the DC motor, where the control device has a rotary pickup arranged on the DC motor to record the actual rotational speed of a motor drive shaft. At the same time, motor rotational speed can be controlled usage-dependently in such a way that a constant test tape speed and therefore a constant test provision time are achieved. Direct recording of the rotation of the motor drive shaft allows the required accuracy of the control with a short dead time. Methods also are provided for operating such hand-held analytical devices.

The devices and methods are useful in a variety of applications such as, for example, measuring analyte concentrations in body fluids such as blood sugars.

Devices and Methods

Devices incorporating the inventive concept include a hand-held device for blood sugar testing. An exemplary hand-held device is shown in FIG. 1, which can be held in the hand of a user and can be used for rapid blood sugar measurements in situ. In this manner, the device 10 includes a housing 12, shown without a lid, with a tape drive 14 and a control device 16 acting thereon for controlling tape transport of a test tape cassette 18 changeable as a disposable means.

The test tape cassette 18, represented without a cover, contains a test tape 20 that is provided in sections with analytical aids 22 such as dry chemical test zones to which blood, or another bodily fluid, can be applied in the region of a tip around which the tape passes, as an application site 24, on their free front side. At the same time, a measurement may be carried out on the rear of the analytical aid 22 instantaneously or currently being used, by means of a photometric measuring unit (not shown). In this manner, the test tape 20 can be wound by means of the tape drive 14 out of a sealed storage chamber 25, from a stock spool 26 located therein, onto a take-up spool 28 so that the mutually separated analytical aids 22 can be sequentially brought for use at the application site 24 for successive tests. Thus, only the take-up spool 28 need be driven by means of the tape drive 14 coupled by means of a driver pin. It is also conceivable to use recess elements or integrated recess/test elements as analytical aids on a test tape.

The tape drive 14 includes a motor 30 formed as a high-speed, low-power DC motor and downstream step-down gearing 34, which can include a worm wheel seated on the motor drive shaft 32 and a multistage spur wheel gear 36. With an angular frequency of the motor 30 in the range of about 600 rad/s to about 1000 rad/s, the spool rotational speed of the take-up spool 28 can be reduced to less than 1 rev/s, so that the required torque is provided in an energy-efficient and compact design, so as also to ensure that the tape is pulled through the seal of the storage chamber 25.

As used herein, "about" means within a statistically meaningful range of a value or values such as a stated concentration, length, molecular weight, pH, speed, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

With the control device 16, it is possible to compensate for large rotational speed variances inherent in the design of low-power DC motors to avoid excessive tensioning of the test tape 20 and to ensure a predetermined provision time of an unused analytical aid 22 in, for example, a range from about 5 s to about 10 s. Thus, it should be taken into account that the analytical aids 22 located on the unused section of the test tape 20 in the storage chamber 25 are respectively not unwound individually until so required by the user to avoid detrimental environmental effects on the sensitive test chemicals. Besides compensation for the motor rotational speed variances for a constant test provision time, the control device 16 also can compensate for rotational speed variations that may be caused by design-related differences of the test tape cassettes 18 by, for example, tolerance-affected frictional resistances of the spools 26, 28.

As shown in the detail enlargement in the lower left of FIG. 1 in axial plan view of a motor shaft 32, the control device 16 includes a rotary pickup 38 arranged on the DC motor 30 to record the actual rotational speed of the motor drive shaft 32. In the exemplary embodiment shown, this is formed as an optoelectronic encoder 40, such as a vaned wheel seated in a rotationally fixed manner on the motor drive shaft in interaction with a four-vaned fork light barrier 44 arranged fixed with respect to the device and enclosing the vaned wheel on both sides. The vaned wheel also may be applied or formed on a gearing component seated in a rotationally fixed manner on the motor drive shaft 32, for example, the worm wheel 34.

Figure 2:
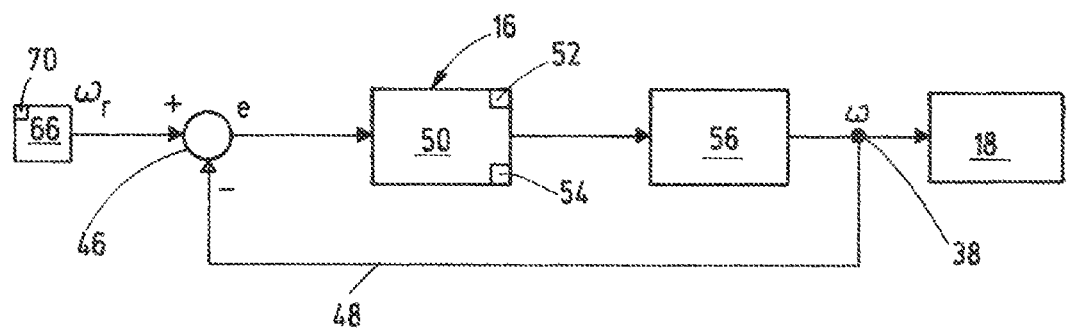
FIG. 2 shows an exemplary block diagram of a control device for a tape drive.

FIG. 2 shows the closed control loop of the control device 16 in a block diagram. A comparator 46 forms a control difference (e) between a setpoint rotational speed ($n_r$) or setpoint angular frequency ($\omega_r$; in general: $n=\omega/2\pi$) and the actual angular frequency ($\omega$) recorded on the motor shaft 32 by means of the rotary pickup 38 and fed back via a feedback branch 48. A control processor 50, to which the control difference e is applied on the input side, ensures reduction of the control difference. To this end, the control processor 50 includes a proportional element 52 and an integral element 54, expediently in the form of a software routine. On the output side, the control processor 50 is coupled to an actuating element 56, which as a pulse-width modulator drives the DC motor 30 with a pulse-width modulated DC voltage. The subsequent multi-stage spur wheel gearing 36 (e.g., toothed drivetrain) converts the drive rotation substantially without discrepancy into a translation of the test tape 20 in the tape cassette 18.

Figure 3:
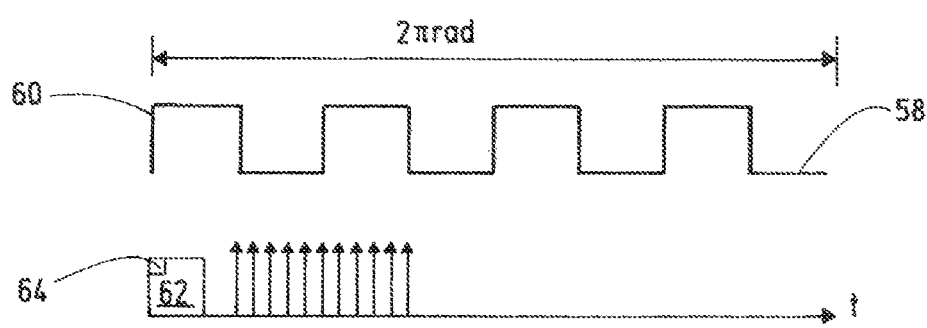
FIG. 3 shows an exemplary time diagram of output signals of a rotary pickup over clock pulses of a time clock generator.

FIG. 3 shows a determination of actual rotational speed (n) from the output signal 58 of the fork light barrier 44. During a revolution of an interrupter 42, such as the four-vaned wheel, with the period $T=2\pi$ rad, four pulses 60 are generated by corresponding light barrier interruptions. A symbolically represented clock generator 62 for generating time clock pulses of clock duration d, in conjunction with a digital counter 64, makes it possible to determine the pulse number i between two trailing edges of output signal 58. From this, the actual rotational speed n or actual angular frequency $\omega$ is given according to equation (1):

$$\omega(\text{rad/s}) = \frac{\frac{1}{4} * 2\pi}{i * d}. \qquad (1)$$

In this method, the rotational speed determination becomes more inaccurate with an increasing angular velocity. With a maximum angular velocity, corresponding to requirements, of $\omega=1128$ rad/s, the counter output will correspondingly determine a pulse number $i=1392$ with a counter tolerance of ±1. This entails a minimum rotational speed determination accuracy of ±0.07%, which is sufficient for the desired accuracy of the rotational speed control. In a configuration of the control elements 52, 54 which is known to one of skill in the art, it is therefore possible to achieve a tape speed of the test tape 20 of about 15±2 mm/s with an adjustment time in the range of from about 0.1 s to about 0.25 s.

By means of a setpoint value generator 66 (FIG. 2) of the control device 16, the setpoint rotational speed is established in accordance with a constant provision time for the respective provision of the analytical aids 22. Expediently, to this end, the tape winding diameter on the take-up spool 28, which determines the tape speed and increases with increasing aid usage, is taken into account by the current test number i of the continuously numbered analytical aids 22. The current test number i is stored in a storage means 68 applied on the test tape cassette 18, for example, an RFID chip (FIG. 1) and fed into the setpoint value generator 66. The latter contains a setpoint value memory 70, in which a value of the angular velocity ($\omega$) to be adjusted is respectively assigned to the test number i for the fifty test zones distributed on the test tape 20 according to Table 1 below.

TABLE 1

| i | Ω (rad/s) | i | Ω (rad/s) | i | Ω (rad/s) | i | Ω (rad/s) | i | Ω (rad/s) |
|---|---|---|---|---|---|---|---|---|---|
| 1 | 985 | 11 | 883 | 21 | 799 | 31 | 731 | 41 | 672 |
| 2 | 974 | 12 | 874 | 22 | 792 | 32 | 724 | 42 | 667 |
| 3 | 964 | 13 | 865 | 23 | 785 | 33 | 718 | 43 | 662 |
| 4 | 953 | 14 | 856 | 24 | 778 | 34 | 712 | 44 | 657 |
| 5 | 942 | 15 | 848 | 25 | 770 | 35 | 706 | 45 | 652 |
| 6 | 931 | 16 | 839 | 26 | 763 | 36 | 700 | 46 | 647 |
| 7 | 922 | 17 | 831 | 27 | 757 | 37 | 694 | 47 | 642 |
| 8 | 912 | 18 | 822 | 28 | 750 | 38 | 689 | 48 | 637 |
| 9 | 902 | 19 | 815 | 29 | 743 | 39 | 684 | 49 | 632 |
| 10 | 892 | 20 | 807 | 30 | 737 | 40 | 678 | 50 | 627 |

Besides the analytical aids 22, function zones 72 also may be provided on the respective sections of the test tape 20, which permit calibration of the photometric measurement unit or accurate tape positioning for different functions. For tape positioning, the function zones 72 are sampled by means of an optical tape sensor that is separate from the photometric measurement unit and comprises a photo-LED for illumination and a photo-transistor for recording the reflection, in the manner of a light barrier. For example, when a white function zone passes through, a square-wave signal with leading and trailing signal edges is recorded, the signal width being dependent on the length of the function zone (as seen in the longitudinal direction of the tape) and its transport speed. For further details of such function zones and their use, reference is made to EP Patent Application No. 2221608.

The control device 16, and in particular the rotary pickup 38, may be used for length recording of the various function zones. The length recording may be used as an additional control criterion, for example, to recover the current position in the event of a device malfunction.

In the case of defined tape speed control by means of the control device, the function zone length may be determined in a particularly straightforward way by an accumulative numerical value of time clock pulses of the clock generator 62 between the aforementioned signal edges when the respective function zone 72 passes through.

The rotary pickup 38 also may be used to directly record a dimension (L) for the function zone 72 length itself in the event of a varying rotational speed. In this case, equation (2) applies:

$$L = u * 2\pi R \quad (2),$$

where u denotes the revolutions of the take-up spool 28 and R denotes its tape winding diameter thereof. Since the ratio of the motor rotational speed n and the spool rotational speed u is determined by the gearing transmission ratio v, the number Pi of pulses 60 of the rotary pickup 38 between the signal edges when the respective function zone 72 passes through gives equation (3):

$$L = Pi * 2\pi R / 4v \quad (3).$$

Thus, when the pulse number Pi of the fork light barrier 44 is recorded directly and the tape winding diameter is known with the aid of the test number, the length L of the relevant function zone 72 can be derived directly.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS

- 10. hand-held analytical device
- 12. housing
- 14. tape drive
- 16. control device
- 18. test tape cassette
- 20. test tape
- 22. analytical aids
- 24. application site
- 25. storage chamber
- 26. stock spool
- 28. take-up spool
- 30. DC motor
- 32. motor drive shaft
- 34. step-down gearing
- 36. multi-stage spur wheel gearing
- 38. rotary pickup
- 40. optoelectronic encoder
- 42. interrupter
- 44. light barrier
- 46. comparator
- 48. feedback branch
- 50. control processor
- 52. proportional control element
- 54. integral control element
- 56. actuating element
- 58. output signal
- 60. pulses
- 62. clock generator
- 64. counter
- 66. setpoint value generator
- 68. storage means
- 70. setpoint value memory
- 72. function zones

The invention claimed is:

1. A hand-held analytical device comprising:
   a replaceable test tape cassette comprising a test tape with a plurality of consecutive analytical aids; and
   a tape drive comprising:
      a DC motor and gearing that can be coupled to the test tape cassette for successively providing the analytical aids, and
      a control device for controlling rotational speed of the DC motor, wherein the control device comprises a rotary pickup arranged on the DC motor to record actual rotational speed of a motor drive shaft, and wherein the rotary pickup comprises an interrupter seated in a rotationally fixed manner on the motor drive shaft and a light barrier fixed to the device and interacting with the interrupter.

2. The hand-held device of claim 1, wherein the rotary pickup comprises an optoelectronic encoder for optically sampling rotation of the motor drive shaft while generating a rate of electrical pulses proportional to rotational speed as an output signal.

3. The hand-held device of claim 1, wherein the interrupter is a vaned wheel or a perforated disk and the light barrier is a fork light barrier.

4. The hand-held device of claim 1 further comprising a clock generator for generating time clock pulses and a counter for counting time clock pulses between two signal edges of an output signal of the rotary pickup.

5. The hand-held device of claim 1, wherein the control device further comprises a comparator for forming a control difference between the actual rotational speed and a setpoint rotational speed specified as a control variable.

6. The hand-held device of claim 1, wherein the control device further comprises a control processor to which a control difference can be applied on an input side for adjusting a setpoint rotational speed in a closed control loop.

7. The hand-held device of claim 6, wherein the control processor comprises at least one proportional control element and at least one integral control element formed by a software routine.

8. The hand-held device of claim 1, wherein the control device further comprises a pulse-width modulator as an actuating element for driving the DC motor with a pulse-width modulated DC voltage.

9. The hand-held device of claim 1, wherein the control device achieves a tape speed of the test tape of about 15±2 mm/s with an adjustment time in a range from about 0.1 s to about 0.25 s.

10. The hand-held device of claim 1, wherein the control device further comprises a setpoint value generator for establishing a setpoint rotational speed in accordance with a constant provision time for provision of the analytical aids.

11. The hand-held device of claim 10, wherein the control device further comprises a setpoint value memory for storing a setpoint value table, in which a value of the setpoint rotational speed of the DC motor is respectively assigned to a test number of the consecutive analytical aids.

12. The hand-held device of claim 11, wherein the test tape cassette further comprises a storage means for usage-dependent storage of a test number of the consecutive analytical aid currently provided.

13. The hand-held device of claim 12, wherein the storage means is a RFID chip.

14. The hand-held device of claim 1, wherein the consecutive analytical aids can be drawn by tape transport from a stock spool shielded from the surroundings and can be provided at an application site.

15. A method for operating a hand-held analytical device in which a test tape provided with a plurality of analytical aids is used in the form of a replaceable test tape cassette in the hand-held device, the method comprising the steps of:
   providing the plurality of analytical aids successively by a tape drive;
   recording actual rotational speed of a motor drive shaft by a rotary pickup of a control device, wherein the rotary pickup is arranged on the DC motor; and
   controlling rotational speed of the DC motor with the control device by forming a control difference between the actual rotational speed and a setpoint rotational speed specified as a control variable, wherein the rotary pickup comprises an interrupter seated in a rotationally fixed manner on the motor drive shaft and a light barrier fixed to the device and interacting with the interrupter.

16. The method of claim 15, wherein the rotary pickup further comprises an optoelectronic encoder that optically samples rotation of the motor drive shaft while generating a rate of electrical pulses proportional to the actual rotational speed.

17. The method of claim 15, wherein the control device achieves a tape speed of the test tape of about 15±2 mm/s with an adjustment time in a range from about 0.1 s to about 0.25 s.

18. The method of claim 15, wherein an angular frequency of the DC motor in a range of about 600 rad/s to about 1000 rad/s.

19. The method of claim 15, wherein a comparator forms the control difference between the actual rotational speed and the setpoint rotational speed.

20. A hand-held analytical device comprising:
a replaceable test tape cassette comprising a test tape with a plurality of consecutive analytical aids; and
a tape drive comprising:
   a DC motor and gearing that can be coupled to the test tape cassette for successively providing the analytical aids, and
   a control device for controlling rotational speed of the DC motor, wherein the control device comprises a rotary pickup arranged on the DC motor to record actual rotational speed of a motor drive shaft, and wherein the control device further comprises a pulse-width modulator as an actuating element for driving the DC motor with a pulse-width modulated DC voltage.

21. A hand-held analytical device comprising:
a replaceable test tape cassette comprising a test tape with a plurality of consecutive analytical aids; and
a tape drive comprising:
   a DC motor and gearing that can be coupled to the test tape cassette for successively providing the analytical aids, and
   a control device for controlling rotational speed of the DC motor, wherein the control device comprises a rotary pickup arranged on the DC motor to record actual rotational speed of a motor drive shaft, wherein the control device further comprises a setpoint value generator for establishing a setpoint rotational speed in accordance with a constant provision time for provision of the analytical aids, and wherein the control device further comprises a setpoint value memory for storing a setpoint value table, in which a value of the setpoint rotational speed of the DC motor is respectively assigned to a test number of the consecutive analytical aids.

* * * * *